Figure 1:
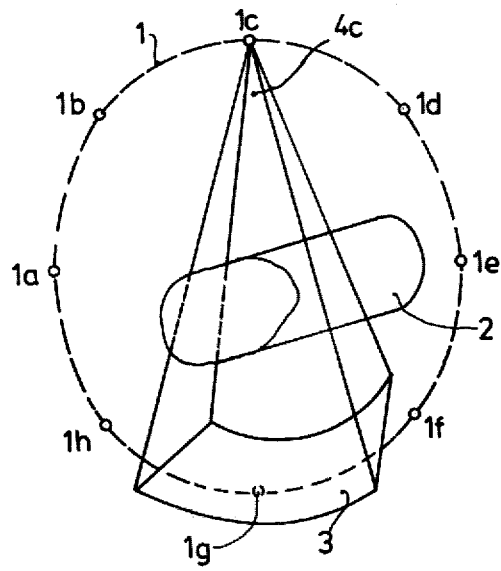

United States Patent [19]

Kowalski

[11] 4,309,615
[45] Jan. 5, 1982

[54] DEVICE FOR DETERMINING THE RADIATION ABSORPTION DISTRIBUTION IN A THREE-DIMENSIONAL EXAMINATION ZONE

[75] Inventor: Günter Kowalski, Rellingen, Fed. Rep. of Germany

[73] Assignee: U.S. Philips Corporation, New York, N.Y.

[21] Appl. No.: 158,189

[22] Filed: Jun. 11, 1980

Related U.S. Application Data

[63] Continuation of Ser. No. 34,306, Apr. 30, 1979, abandoned.

[30] Foreign Application Priority Data

May 2, 1978 [DE] Fed. Rep. of Germany ....... 2819237

[51] Int. Cl.$^3$ ............................................. G03B 41/16
[52] U.S. Cl. ................................................ 250/445 T
[58] Field of Search ........................... 250/445 T, 360

[56] References Cited

U.S. PATENT DOCUMENTS 4,145,614 3/1979 Kowalski .................. 250/445 T
4,160,167 7/1979 Weiss .......................... 250/445 T Primary Examiner—Craig E. Church
Attorney, Agent, or Firm—Thomas A. Briody; Robert T. Mayer; Jack E. Haken

[57] ABSTRACT

A device for determining the radiation absorption distribution in a three-dimensional examination zone which is irradiated from different positions which are situated in one plane and in which radiation sources are present. The device comprises two detector arrays consisting of separate, adjacently arranged detectors, which are situated at a distance from and parallel to each other in a first plane and in a second plane. The device further comprises radiation sources which are situated between the two extreme planes and which are arranged to be rotate around an axis of rotation which extends transversely of said planes. The radiation sources are line-shaped and are arranged parallel to the axis of rotation and diametrically with respect to the axis of rotation opposite a detector array.

6 Claims, 7 Drawing Figures

DEVICE FOR DETERMINING THE RADIATION ABSORPTION DISTRIBUTION IN A THREE-DIMENSIONAL EXAMINATION ZONE

This is a continuation, of application Ser. No. 34,306, filed Apr. 30, 1979 now abandoned.

This invention relates to a device for determining a radiation absorption distribution in a three-dimensional examination zone, comprising various radiation sources which are situated in one plane and which serve for irradiating the examination zone from different directions, comprising detectors for detecting the radiation having passed the examination zone and for supplying sets of output signals which are characteristic of the absorption of the radiation, and also comprising an arithmetic device for reconstructing the radiation absorption distribution on the basis of the output signals.

A device of this kind is known from a publication by R. E. Sturm et al in "Cardiovascular Imaging and Image Processing, Theory and Practice 1975", Vol. 72, pages 103 to 122. This device enables the reconstruction of an absorption distribution in a three-dimensional examination zone which is irradiated from a large number of positions situated in one plane. The three-dimensional absorption distribution is reconstructed from the sets of output signals measured therein by the detector device. The detector device is of a two-dimensional type and extends perpendicularly to the connecting line between the radiation source device and the detector device. However, for the determination of the three-dimensional absorption distribution reconstruction difficulties arise if the angle of aperture of the radiation beam is excessively large in a direction perpendicular to said connecting line.

In that case, different areas in the examination zone (body) are dissimilarly irradiated in different directions. Thus, in comparison with the quantity of data obtained as regards the structures in the central zone between the edge areas, comparatively little information is obtained concerning structures which are situated in an edge area.

Also known are computer tomography devices in which the radiation absorption distribution is reconstructed in a (two-dimensional) plane (German Offenlegungsschrift 24 42 809) and in which the examination zone is irradiated by an X-ray source wherefrom an X-ray beam is stopped which is flat in one direction, perpendicularly to the plane of examination, said beam irradiating the complete plane of examination and being measured by a detector device which is arranged in the flat radiation beam at the other side of the plane of examination. The X-ray source/detector assembly is then rotated around an axis which extends perpendicularly to the plane of examination and the absorption distribution in the plane is reconstructed from the output signals of the detector device thus obtained.

In a device of this kind, the absorption distribution can be determined in only one layer or, if a second detector device is provided, in only two adjacently situated layers of a three-dimensional object. When an apparatus of this kind is used for the successive scanning of adjacently situated layers, these layers, however, will not adjoin if the object (body) to be examined moves during the successive scans.

The invention has for its object to provide a device for determining the absorption distribution in a three-dimensional examination zone in which the difficulties encountered during the reconstruction on the basis of the data from the dissimilarly irradiated areas of the examination zone are mitigated.

To this end, the device in accordance with the invention is characterized in that between a first plane and a second plane, situated at a distance from and parallel to each other, radiation sources are arranged in a radiation source plane which is equidistant from an axis of rotation, the axis of rotation extending transversely of said first two planes and the radiation sources being adjacently situated parallel to and rotatable around the axis of rotation, the detector device comprising at least two detector arrays which extend transversely of the axis of rotation and which consist of separate, adjacently situated detectors, said detector arrays being arranged in said first two planes and diametrically opposite the radiation sources with respect to the axis of rotation.

It is thus achieved that the examination zone, or a body present therein, is substantially homogeneously irradiated, so that output signals having the same signal-to-noise ratio are obtained from each part of the examination zone.

A further result of this homogeneous irradiation consists in that the quantity of information obtained as regards the absorption of a point inside the examination zone is independent to a high degree of the position of this point inside the examination zone. This particularly facilitates the reconstruction. A further advantage consists in that the examination zone is a space which can be simply mathematically defined (for example, a cylindrical surface bounded by parallel planes). Thus, the body can be attractively described by a cylinder coordinate system for the reconstruction.

A further embodiment of a device in accordance with the invention is characterized in that there is provided a holder on which a support is provided which is rotatable around the axis of rotation, said support accommodating two radiation source arrays which are remote from each other in the direction of rotation and which are arranged on a straight line, said source arrays extending from the first plane to the second plane, the holder also accommodating two identical detector arrays each of which are to be irradiated by one radiation source array and which are arranged in the form of a ring, the axis of rotation extending through the centres of the rings.

It is thus achieved that instead of two-dimensional detector devices, use can be made of only one-dimensional arrays of detectors, for example, stationary rings of detectors.

An embodiment of the device in accordance with the invention will be described in detail hereinafter with reference to the accompanying diagrammatic drawing.

Figure 2:
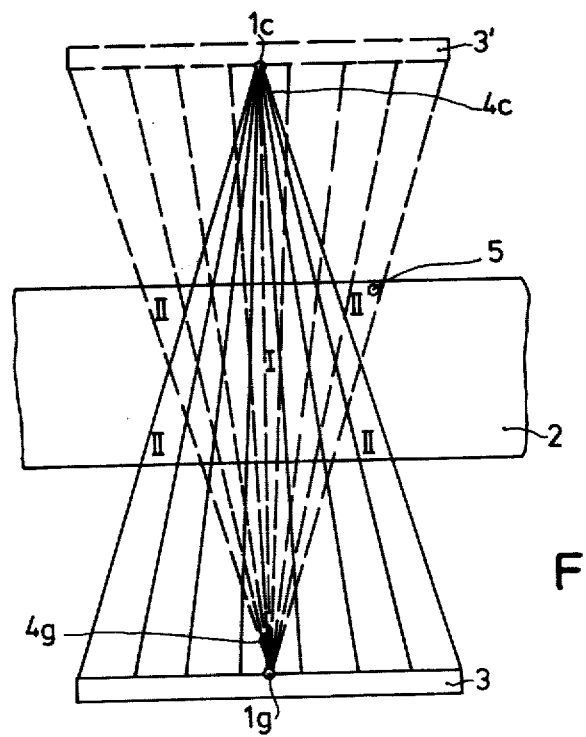
Figure 3:
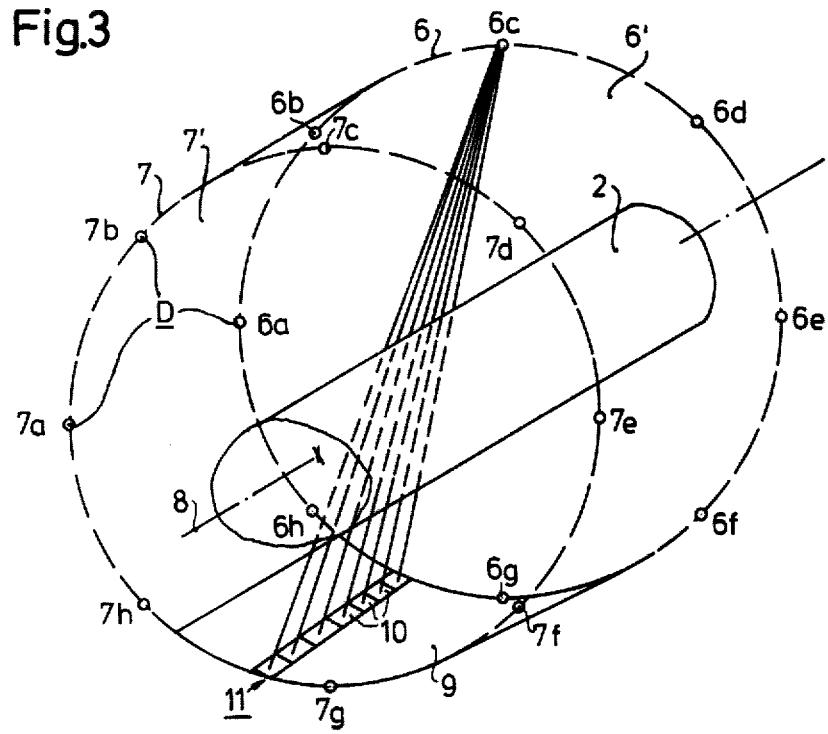
Figure 4:
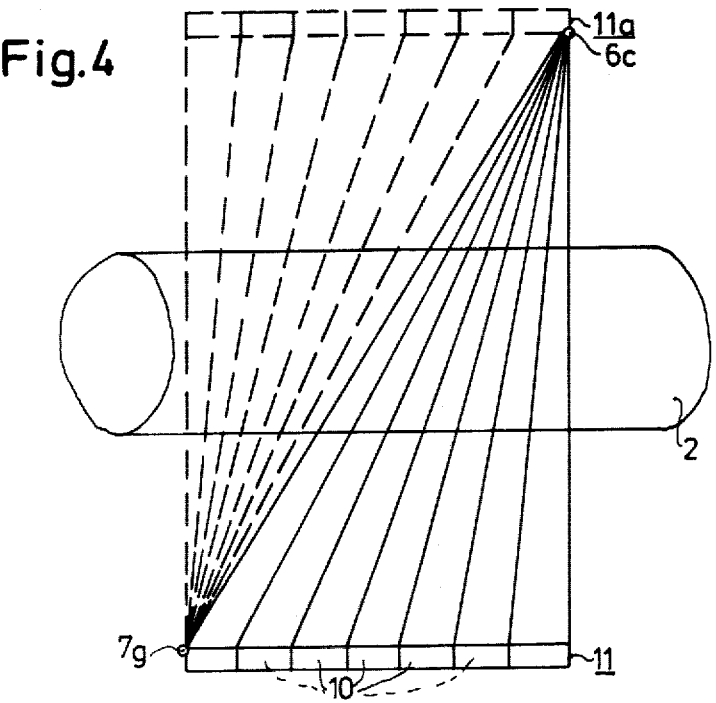
Figure 5:
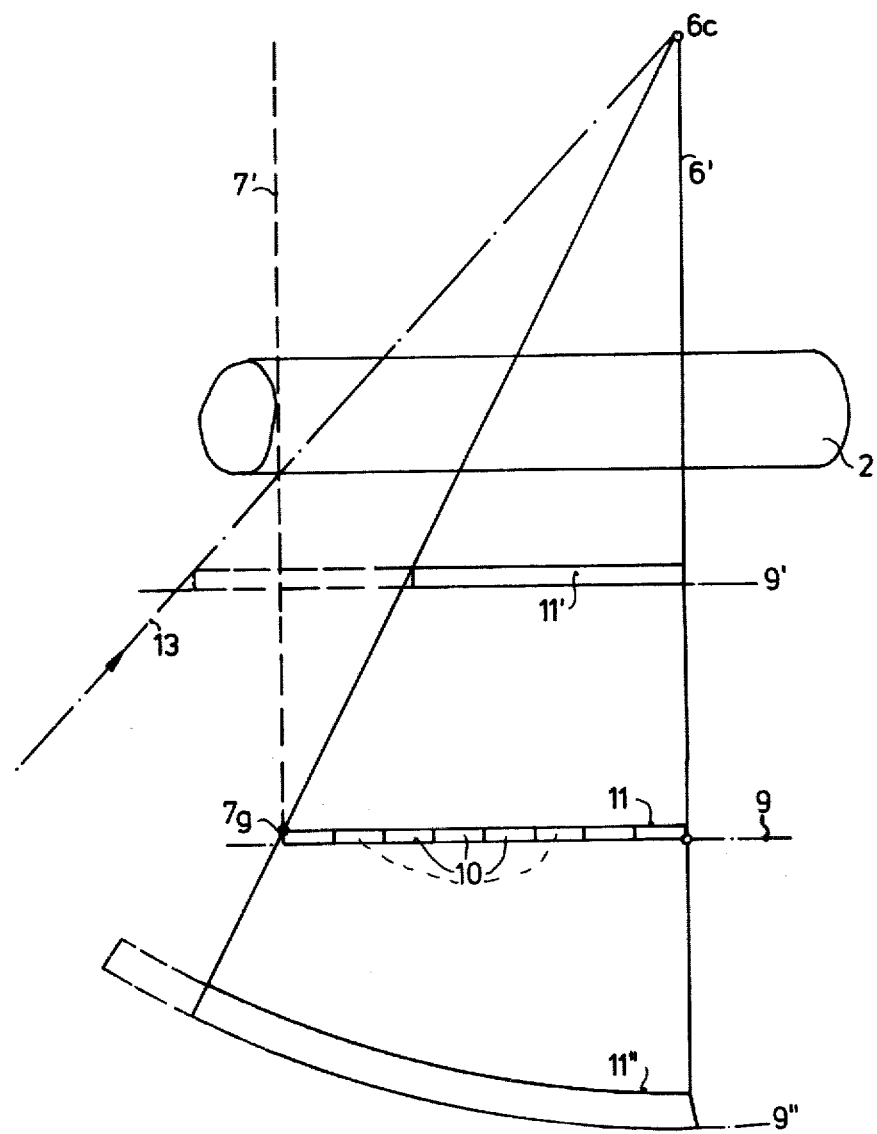
Figure 6:
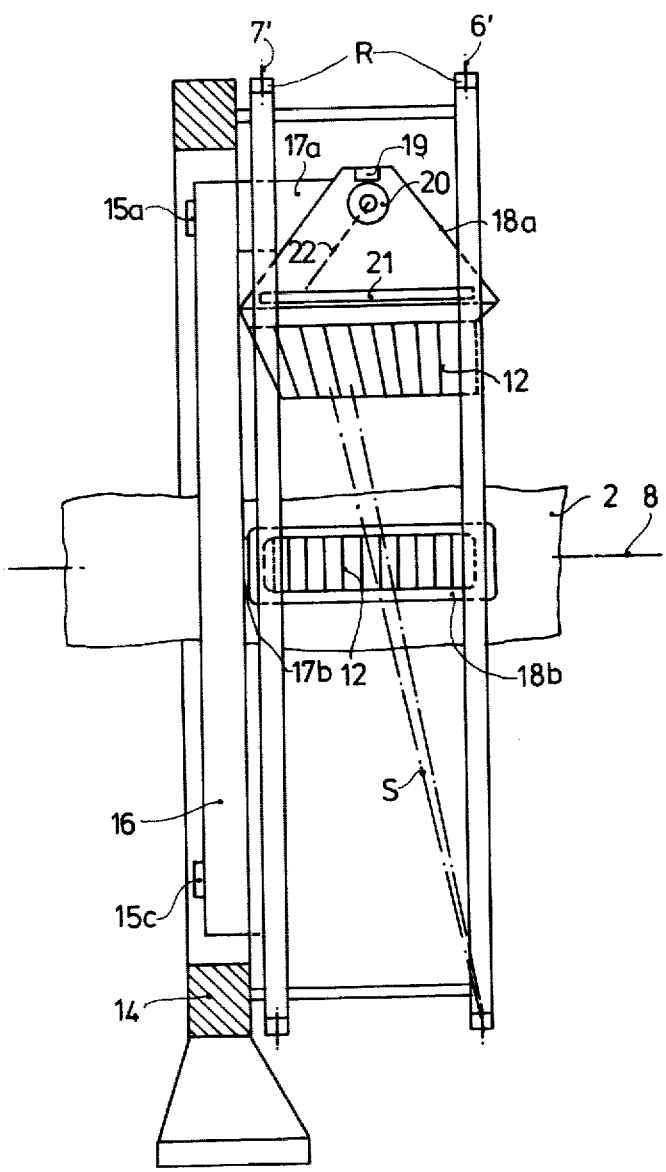
Figure 7:
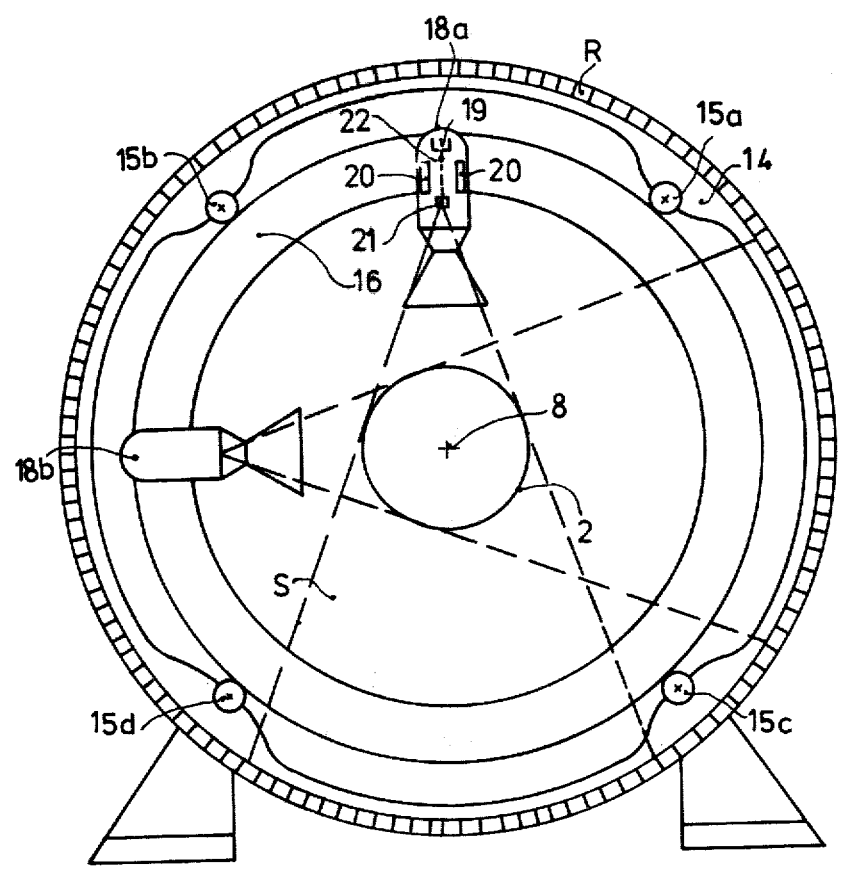

FIG. 1 is a perspective view of a geometrical configuration of a known device,

FIG. 2 is a sectional view, taken in a plane perpendicular to the first plane, of a gecmetrical configuration of a known device, FIG. 3 is a perspective view of a geometrical configuration of a device in accordance with the invention, FIG. 4 is a sectional view, taken perpendicularly to both planes, of a device in accordance with the invention, FIG. 5 shows various feasible geometries of the radiation source arrays, FIG. 6 is a side elevation of an embodiment of a device in accordance with the invention, and FIG. 7 is a front view of the embodiment shown in FIG. 6.

The reference numeral 1 in FIG. 1, which is a perspective view of a geometrical configuration of a known device, denotes a circle on which the positions 1a to 1h wherefrom the body 2 is irradiated during the examination are situated. In the device as described in the publication by R. E. Sturm, the radiation is generated by a large number of radiation sources (X-ray tubes) which are situated in the positions 1a to 1h; however, use can alternatively be made of a single radiation source which is successively moved to the positions 1a to 1h. For the sake of simplicity, the drawing shows only eight different positions, but a substantially larger number of positions are required in order to obtain adequate spatial resolution. The reference numeral 4c in FIG. 1 denotes a radiation beam which is stopped in the position 1c of a radiation source (not shown). This beam is shaped as a pyramid, and the plane in which the circle 1 is situated is a symmetry plane of this pyramid. The radiation beam is incident on a two-dimensional detector device 3 which is situated opposite the position 1c. This device is curved around the central axis of the circle 1 and extends perpendicularly to the plane containing the circle 1.

FIG. 2 shows a geometrical configuration in a plane which extends perpendicularly to the circle 1 and through the centre of the examination zone or the body 2, the radiation beam 4c stopped in the position 1c as well as the detector device 3 is denoted by non-interrupted lines, while the radiation beam 4g stopped in the position 1g and the associated detector position 3' are denoted by broken lines. It is clearly shown that there are edge regions II which are irradiated only in given positions of the X-ray source and a central region I which is substantially always irradiated. In the edge regions II there are points, such as the point 5, which are irradiated in only one position of the radiation source (N), in this case when the radiation source occupies the position 1g. The other radiation beams, stopped in the further positions, do not irradiate this point 5. Other details situated in the edge regions II can substantially hamper the reconstruction, because only little information concerning these details is measured.

FIGS. 3 and 4 show geometrical proportions of a device in accordance with the invention. Instead of one circle, two equally large circles 6, 7 which are situated in two planes extending parallel to each other are imagined, said circles having a common central axis 8 (axis of rotation). On these circles 6, 7 there are arranged detector arrays comprising separate detectors D, only eight detectors D with detector positions 6a to 6h, 7a to 7h being shown. Generally, a substantially larger number of detectors D (between 500 and 2000) are arranged on each circle 6, 7, so that arc-shaped or ring-shaped detector arrays (FIGS. 5, 6) are formed. On an imaginary cylindrical surface 9 (only partly shown) which connects the circles 6 and 7 there are provided radiation sources 10 which are adjacently arranged on a straight line and which are successively flashed, said sources forming a radiation source array 11 which extends parallel to the axis of rotation 8. For the sake of clarity, the drawing shows only one radiation source array 11. Obviously, the cylindrical surface 9 may be occupied by a large number of parallel extending radiation source arrays 11. A radiation source array 11, of course, can also be rotated around the axis of rotation 8, so that the radiation sources 10 can successively occupy different positions on the cylindrical surface 9. Obviously a radiation source array can alternatively be formed by an elongate, linear anode of an X-ray tube which is scanned by an electron beam which moves on the cylindrical surface 9 parallel to the direction of the central axis 8, so that the source successively occupies the necessary positions between the circles 6 and 7.

The radiation of the individual radiation sources 10 to be successively flashed in the time is directed so that a radiation source array 11 strikes each time only one detector array (on the circle 6 or 7). This is achieved by means of suitable collimators 12 (see FIG. 7). The radiation emerging from a radiation source 10 then reaches a large number of adjacently arranged detectors D of a detector array, for example, the detectors D with the detector positions 6b to 6d shown in FIG. 3. For the sake of clarity only the successive radiation of the radiation sources 10 which reaches the detector D with the position 6c is shown. By a suitable collimator arrangement (not shown) in front of the detectors D and/or the radiation sources 10, it can also be ensured that at least a few radiation sources 10 (the radiation source positions) of a radiation source array 12 may emit radiation simultaneously, the different radiation beams, however, then reaching different detectors D of a detector array. FIG. 4 shows separate radiation beams (denoted by broken lines and non-interrupted lines) which are produced when the radiation penetrating the body 2 is measured by the detectors D with the positions 6c and 7g. The radiation source arrays 11 and 11a are shown in two different, diametrically oppositely situated positions and each source array strikes a detector array. It is clearly shown that a thick slice of the body 2 is substantially homogeneously irradiated and that each point in the examination zone, which may be defined as a cylindrical surface bounded by parallel planes which is situated between the circles 6 and 7, is covered by the radiation. For a large number of directions, corresponding to the number of detectors D present on a circle 6, 7, such a pair of detector positions 6c, 7g shifted through 180° with respect to each other, can be indicated.

FIG. 5 again shows the position 6c of a detector which is irradiated by separate radiation sources 10 of a radiation source array 11. It is not important whether the radiation source array 11 is situated on the cylindrical surface 9 or on a projection 9', 9" of this surface. In all cases equivalent measuring values are obtained. Similarly, an extension of the radiation source array 11, for example, see 11', 11", does not have a disturbing effect and may even be useful (see the area of the radiation source arrays 11', 11" denoted by broken lines) as long as a measuring beam 13 which bounds the radiation beam passes through the planes 6' and 7' defined by the detector rings 6 and 7, respectively, prior to entering the body 2 to be examined.

It is not necessary per se that each position on the one circle 6 is associated with a position on the other circle 7 which has been rotated exactly through 180° with respect to the axis of rotation 8 of the circles 6, 7. In that case, the configuration shown in FIG. 4 is not completely realized, because there is not directly oppositely situated position, but there are always two positions which are arranged almost one opposite the other. Because usually very many positions must be present on a circle 6, 7 no errors are introduced thereby.

It is not necessary either for the positions to be distributed over the entire circumference of the two circles 6, 7; it is generally sufficient that only a part of a circle 6, 7 which is larger than one half circle is occupied by such positions, provided that for each position on the one circle a complementary position, i.e a position rotated through approximately 180°, can be indicated on the other circle.

Within the scope of the present invention, it is not important whether the detector rings R are fully occupied by detectors D or whether a few detectors D are placed in the required position by mechanical movement. It is not important either whether a large number of separate radiation sources 10 are provided on the source surface (cylindrical surface 9) or whether a few radiation sources emit radiation from a large number of positions reached by mechanical movement.

A sensible compromise is found by providing two detector rings R which consist of separate, adjacently situated detectors D, for example, scintillators and photo diodes. The radiation source positions are then changed by mechanical movement of the radiation source array 11 in the circumferential direction, whilst the flashing of the individual radiation sources 10 is electronically realized.

The FIGS. 6 and 7 are a side elevation and a front view, respectively, of a device in accordance with the invention. The two detector rings R, situated in the planes 6' and 7' are secured on a holding ring 14. A rotatable support 16 is retained by the bearings 15a to 15d, X-ray sources 18a and 18b being secured to said support by means of two arms 17a and 17b. Collimators 12 are rigidly arranged in front of the X-ray sources 18a and 18b, said collimators collimating the X-radiation generated on the anode 21 to form a radiation beam S (denoted by broken lines) so that the radiation of the radiation source 18a reaches only the detector ring R situated in the plane 6', while the radiation of the radiation source 18b reaches only the detector ring R situated in the plane 7'. These collimators are required to prevent the body 2 from being exposed to excess X-radiation which is not used for the measurement. The radiation sources 18a and 18b have the same construction and consist of an electron source 19, deflection coils 20 and a linear anode 21 on which X-radiation is generated by exposure to the electron beam 22. The focus is quickly moved to and fro on the anode 21 by suitable deflection voltages, whilst the radiation sources 18a and 18b mechanically rotate around the body 2 in the circumferential direction. A uniform distribution of radiation source positions (focus positions) on the cylindrical surface 9 is obtained by superposition of the mechanical movement and the electrical movement of the focus of the X-ray sources 18a and 18b. In a modified embodiment of the device, it is only necessary to use part of the two detector rings R because this part rotates permanently with the radiation source 18a, 18b so that it is always situated opposite the associated radiation source 18a, 18b.

What is claimed is:

1. In a device for determining a radiation absorption distribution in a three-dimensional examination zone comprising: radiation sources which are situated in one plane and which irradiate the examination zone from different directions; detectors which detect the radiation which has passed through the examination zone and supply sets of output signals which are characteristic of the absorption of the radiation; and an arithmetic device which reconstructs the radiation absorption distribution on the basis of the output signals, the improvement wherein the radiation sources are arranged in a radiation source plane which is equidistant from an axis of rotation, the axis of rotation extending transversely to a first plane and a second plane, situated at a distance from and parallel to each other, the radiation sources being adjacently situated parallel to and rotatable around the axis of rotation and the detectors comprise at least two detector arrays which extend transversely to the axis of rotation and which consist of separate, adjacently situated detectors, said detector arrays being arranged in the said two planes, diametrically opposite the radiation sources with respect to the axis of rotation.

2. A device as claimed in claim 1, wherein the detector array is a ring of detectors.

3. A device as claimed in claim 2, further comprising a holder; a support disposed on the holder which support is rotatable around the axis of rotation; two radiation source arrays situated on the support, which arrays are remote from each other in a direction of rotation and which are arranged on a straight line, said source arrays extending from the first plane to the second plane; and two identical detector array rings each of which rings is irradiated by one radiation source array, the axis of rotation extending through the centers of the rings.

4. A device as claimed in claims 1, 2 or 3, further comprising collimator means associated with each radiation source which direct the radiation onto a part of the associated ring of detectors.

5. A device as claimed in claims 1, 2 or 3 wherein the radiation sources comprise X-ray tubes, the X-ray emission point in which is movable along a rod-shaped anode by deflection of an electron beam.

6. A device as claimed in claim 4 wherein the radiation sources comprise X-ray tubes, the X-ray emission point in which is movable along a rod-shaped anode by deflection of an electron beam.

* * * * *